United States Patent
Garde

(10) Patent No.: US 10,869,978 B2
(45) Date of Patent: Dec. 22, 2020

(54) METHOD OF $CO_2$ MEASUREMENT DURING NON-INVASIVE VENTILATION

(71) Applicant: KONINKLIJKE PHILIPS N.V., Eindhoven (NL)

(72) Inventor: Smita Garde, Irvine, CA (US)

(73) Assignee: Koninklijke Philips N.V., Eindhoven (NL)

( * ) Notice: Subject to any disclaimer, the term of this patent is extended or adjusted under 35 U.S.C. 154(b) by 214 days.

(21) Appl. No.: 15/780,432

(22) PCT Filed: Nov. 24, 2016

(86) PCT No.: PCT/IB2016/057086
§ 371 (c)(1),
(2) Date: May 31, 2018

(87) PCT Pub. No.: WO2017/093862
PCT Pub. Date: Jun. 8, 2017

(65) Prior Publication Data
US 2018/0361091 A1 Dec. 20, 2018

Related U.S. Application Data

(60) Provisional application No. 62/261,924, filed on Dec. 2, 2015.

(51) Int. Cl.
*A61M 16/00* (2006.01)
*A61M 16/06* (2006.01)
*A61M 16/08* (2006.01)

(52) U.S. Cl.
CPC ...... *A61M 16/024* (2017.08); *A61M 16/0066* (2013.01); *A61M 16/06* (2013.01);
(Continued)

(58) Field of Classification Search
CPC ............ A61M 16/0066; A61M 16/024; A61M 16/06; A61M 16/08; A61M 16/085;
(Continued)

(56) References Cited

U.S. PATENT DOCUMENTS 6,371,113 B1 4/2002 Tobia et al.
8,985,107 B2 3/2015 Viertio-Oja et al.
(Continued)

FOREIGN PATENT DOCUMENTS

WO 0226287 A2 4/2002
WO 2011070472 A1 6/2011

OTHER PUBLICATIONS

Google.com website dictionary definition for "Breath" (2020) (Year: 2020).*

*Primary Examiner* — Timothy A Stanis
*Assistant Examiner* — Charles M Vivian
(74) *Attorney, Agent, or Firm* — Daniel H. Brean

(57) ABSTRACT

A method for measuring a patient's expired $CO_2$ level in a non-invasive ventilator system while maintaining a positive inspiratory pressure. The method includes the steps of: receiving, by the non-invasive ventilator system, a signal comprising an instruction to obtain a $CO_2$ measurement from a patient; lowering, by the non-invasive ventilator system in response to the signal, the expiratory positive airway pressure from a first, higher level to a second, lower level for a first time period comprising one or more breaths; obtaining, by a $CO_2$ sensor, a $CO_2$ measurement during the first time period; and returning, after the first time period, the expiratory positive airway pressure to the first, higher level.

16 Claims, 4 Drawing Sheets

(52) U.S. Cl.
CPC ........... *A61M 16/08* (2013.01); *A61M 16/085* (2014.02); *A61M 2016/0015* (2013.01); *A61M 2205/505* (2013.01); *A61M 2205/52* (2013.01); *A61M 2230/432* (2013.01)

(58) Field of Classification Search
CPC .... A61M 2016/0015; A61M 2205/505; A61M 2205/52; A61M 2230/432
See application file for complete search history.

(56) References Cited

U.S. PATENT DOCUMENTS

| | | | |
|---|---|---|---|
| 2012/0234324 A1* | 9/2012 | Orr | A61M 16/00 128/204.22 |
| 2013/0053717 A1* | 2/2013 | Vandine | A61B 5/150992 600/532 |
| 2013/0267863 A1* | 10/2013 | Orr | A61B 5/0836 600/532 |
| 2015/0328417 A1* | 11/2015 | Loser | A61M 16/024 128/204.23 |

* cited by examiner

METHOD OF CO₂ MEASUREMENT DURING NON-INVASIVE VENTILATION

CROSS-REFERENCE TO PRIOR APPLICATIONS

This application is the U.S. National Phase application under 35 U.S.C. § 371 of International Application No. PCT/IB2016/057086, filed on Nov. 24, 2016, which claims the benefit of U.S. Provisional Patent Application No. 62/261,924, filed on Dec. 2, 2015. These applications are hereby incorporated by reference herein.

FIELD OF THE INVENTION

The present disclosure is directed generally to methods and systems for measuring $CO_2$ levels in a non-invasive ventilator system.

BACKGROUND

The most common means of providing critical care ventilation requires intubating patients with an endotracheal tube that seals within the trachea using an inflatable cuff. Intubation offers the best means of clinically managing the airway and maintaining lung inflation, but it introduce significant risks including tissue abrasion, infection, and sedation of the patient due to extreme discomfort. Accordingly, intubation is appropriately called invasive ventilation, and the clinician's decision to intubate must be carefully considered. For a select group of hospitalized patients requiring breathing support, the risks leading to adverse side effects of intubation can outweigh the benefits.

In light of significant risks of invasive ventilation, an alternative approach was developed from home care ventilation that offers the benefit of applying support through the airway, however using a connection by means of a mask over the patient's mouth and nose, or a tracheostomy tube. This approach is called non-invasive positive pressure ventilation, or simply non-invasive ventilation (NIV). For non-invasive ventilation, some leak is expected and often purposely introduced in order to reduce end-tidal $CO_2$ that would otherwise be rebreathed by the patient, since a single limb circuit connects the ventilator to the mask in a non-invasive ventilation system. In comparison, invasive ventilation uses a dual-limb connecting circuit that separately carries exhaled gases, which prevents rebreathing of $CO_2$ in invasive ventilation which therefore requires no leak.

To ensure proper oxygen delivery and to deter conditions such as hypercapnia—an excess concentration of carbon dioxide in the blood—the concentration of $CO_2$ in the system is carefully monitored. The methods for $CO_2$ monitoring during non-invasive ventilation include arterial blood gases (ABGs) for partial pressure of arterial carbon dioxide ($PaCO_2$) measurement or continuous sampling of exhaled flow with a mainstream or a sidestream sensor for end-tidal carbon dioxide ($etCO_2$) measurement. For example, mainstream sensor measurements can be based on the exhaled flow that flows back to the sensor placed between the mask elbow and the exhalation port connected to the patient circuit, for single-limb non-invasive ventilation. For dual-limb non-invasive ventilation, the mainstream sensor can be placed between the non-vented mask port and the patient circuit wye, the wye being the connector that joins the inspiratory and expiratory limbs of a two-limb patient circuit to the patient airway. Alternatively, the sidestream sensor can be connected to the sampling cannula placed under the mask to collect the exhaled flow via the nasal and oral prongs placed at the nares and mouth.

However, the delivery of non-invasive ventilation is usually associated with high leaks around the mask seal on the face, which leads to exhaled gas escaping through the leaks around the mask before a substantial amount reaches the mainstream sensor. The sidestream sensor with its sampling cannula placed in the nares may provide better $CO_2$ measurement, but is affected by the dilution of exhaled flow with the gas flow from the ventilator to maintain expiratory positive airway pressure (EPAP). Additionally, the placement of the cannula under the mask may lead to an increase in the leak around the mask. During single-limb non-invasive ventilation, for example, a minimum EPAP level of approximately four (4) $cmH_2O$, of air, $O_2$, or a mixture thereof, is typically maintained during exhalation to allow the exhaled gas to escape out of the exhalation port(s) and from the leaks around the mask seal on the face. When the leak around the mask is higher, then the ventilator delivers more gas to maintain EPAP and thus more of the exhaled gas escapes out of the exhalation port. As more exhaled gas escapes through mask leaks during higher leak scenarios, hardly any exhaled gas with $CO_2$ reaches the $CO_2$ sensor and the $CO_2$ measurements are erroneous.

Accordingly, there is a need in the art for non-invasive ventilator systems that more precisely measure $CO_2$ levels despite leaks, and while maintaining expiratory positive airway pressure in the system.

SUMMARY OF THE INVENTION

The present disclosure is directed to inventive methods and systems for measuring $CO_2$ levels in a non-invasive ventilator system. Various embodiments and implementations herein are directed to a non-invasive ventilator system that measure $CO_2$ using a standalone or integrated $CO_2$ sensor. To obtain a measurement of $CO_2$ level, the EPAP level of the non-invasive ventilator system is set by the clinician to a lower level, preferably below four $cmH_2O$, for a predetermined number of breaths. During the lowered EPAP level, the $CO_2$ sensor obtains one or more $CO_2$ measurements. After the predetermined number of breaths, the EPAP level is returned to the original EPAP setting.

Generally, in one aspect, a ventilator for measuring a patient's expired $CO_2$ level in a non-invasive ventilator system while maintaining a positive inspiratory pressure is provided. The method includes the steps of: receiving, by the non-invasive ventilator system, a signal including an instruction to obtain a $CO_2$ measurement from a patient; lowering, by the non-invasive ventilator system in response to the signal, the expiratory positive airway pressure from a first, higher level to a second, lower level for a first time period comprising one or more breaths; obtaining, by a $CO_2$ sensor, a $CO_2$ measurement during the first time period; and returning, after the first time period, the expiratory positive airway pressure to the first, higher level.

According to an embodiment, the step of lowering the expiratory positive airway pressure from a first, higher level to a second, lower level comprises sending a control signal to a blower of the non-invasive ventilator.

According to an embodiment, the method includes the step of sending a signal from a controller of the non-invasive ventilator system to the $CO_2$ sensor, the signal comprising instructions to obtain the $CO_2$ measurement during the first time period.

According to an embodiment, the second, lower level is approximately 1 $cmH_2O$.

According to an embodiment, the first period of time is approximately two breaths.

According to an embodiment, the method further includes the step of providing the $CO_2$ measurement to a user.

According to an embodiment, the receiving step includes configuring the non-invasive ventilator system to obtain a $CO_2$ measurement at one of a periodic interval of patient-triggered breaths.

According to a second aspect, a non-invasive ventilator configured to measure a patient's expired $CO_2$ level while maintaining a positive inspiratory pressure is provided. The non-invasive ventilator system includes: a user interface configured to receive, from a user, a signal comprising an instruction to obtain a $CO_2$ measurement from the patient during a first time period comprising one or more breaths; a $CO_2$ sensor configured to obtain one or more expired $CO_2$ measurements from the patient during the first time period; and a controller in communication with the $CO_2$ sensor, the controller configured to lower, in response to the signal, the expiratory positive airway pressure from a first, higher level to a second, lower level for the first time period, and further configured to direct the $CO_2$ sensor to obtain a $CO_2$ measurement during the first time period, and further configured to return, after the first time period, the expiratory positive airway pressure to the first, higher level.

According to an embodiment, the non-invasive ventilator further includes a user interface configured to receive the signal from the user. According to an embodiment, the user interface is a button.

According to an embodiment, the $CO_2$ sensor is an integrated sensor located near a patient interface.

According to an embodiment, the non-invasive ventilator further includes a display screen configured to display the obtained $CO_2$ measurement.

According to a third aspect, a controller of a non-invasive ventilator system configured to measure a patient's expired $CO_2$ level while maintaining a positive inspiratory pressure is provided. The controller is configured to: receive, from a user interface of the non-invasive ventilator system, a signal comprising an instruction to obtain a $CO_2$ measurement from a patient; lower, in response to the signal, the expiratory positive airway pressure of the non-invasive ventilator system from a first, higher level to a second, lower level for a first time period comprising one or more breaths; send a signal to a $CO_2$ sensor of the non-invasive ventilator system, the signal comprising instructions to obtain the $CO_2$ measurement during the first time period; and return, after the first time period, the expiratory positive airway pressure to the first, higher level.

As used herein for purposes of the present disclosure, the term "controller" is used generally to describe various apparatus relating to the operation of a ventilator apparatus, system, or method. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a ventilator system and method. More generally, Applicant has recognized and appreciated that it would be beneficial to provide a non-invasive ventilation system that accurately measures $CO_2$ levels using a standalone or integrated $CO_2$ sensor. To obtain a measurement of $CO_2$ level, the EPAP level of the non-invasive ventilator system is reduced by the clinician for a predetermined number of breaths during which time $CO_2$ measurements are obtained by the $CO_2$ sensor. The system includes a controller, in communication with the $CO_2$ sensor, that controls the EPAP level changes and monitors the number of breaths to determine when to take $CO_2$ measurements and when to return the EPAP to normal levels.

Figure 1:
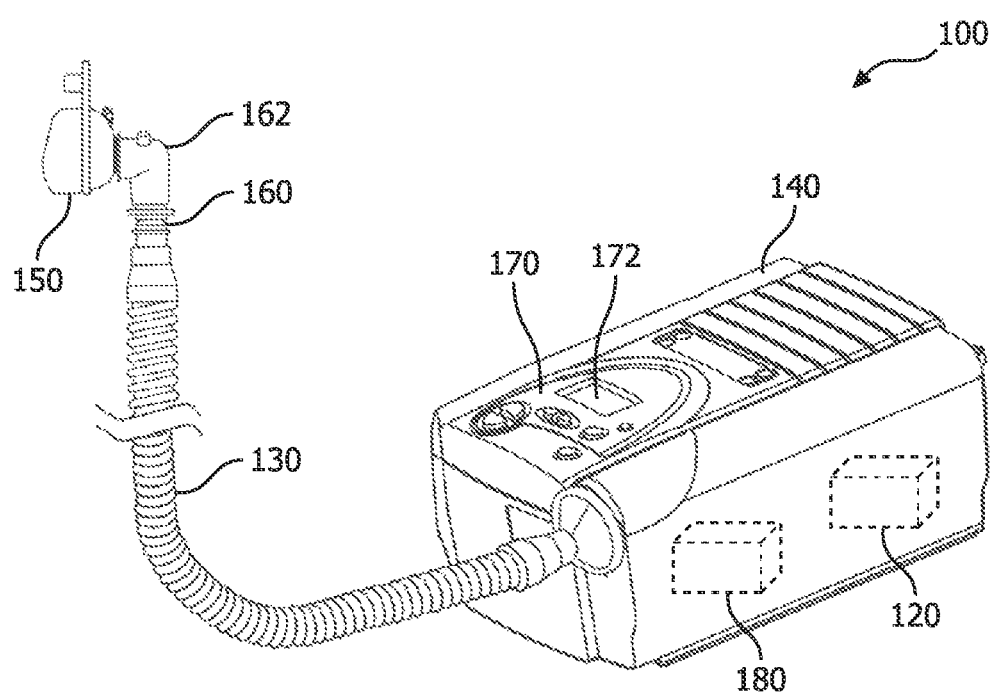
FIG. 1 is a schematic representation of a non-invasive ventilator system in accordance with an embodiment.

Referring to FIG. 1, in one embodiment, is a representation of an example non-invasive ventilation system 100. In this embodiment, the system is a single limb ventilator such that there is a leak flow near the patient connection, and such that patient-exhaled gas has the potential to travel in a reverse direction through the blower during exhalation. The system includes a controller 120, which can be a conventional microprocessor, an application specific integrated circuit (ASIC), a system on chip (SOC), and/or a field-programmable gate arrays (FPGA), among other types of controllers. A controller may be implemented with or without employing a processor, and also may be implemented as a combination of dedicated hardware to perform some functions and a processor (e.g., one or more programmed microprocessors and associated circuitry) to perform other functions.

The controller 120 can be coupled with or otherwise in communication with any needed memory, power supply, I/O devices, control circuitry, and/or other devices necessary for operation of the system according to the embodiments described or otherwise envisioned herein. For example, in various implementations, a processor or controller may be associated with one or more storage media. In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

According to an embodiment, the non-invasive ventilation system includes a tube or tubing 130 that delivers gas from the remote ventilator component 140 to the patient interface 150. Patient interface 150 can be, for example, a face mask that covers all or a portion of the patient's mouth and/or nose. There may be masks of many different sizes to accommodate patients or individuals of different sizes, and/or the mask may be adjustable. As another alternative, patient interface 150 may fit within or on, or otherwise interact with, a tracheostomy tube. Accordingly, the patient interface 150 may be a variety of sizes to accommodate tracheostomies of different shapes and sizes. The patient interface is configured to fit with at least a portion of the patient's airway.

Tubing 130 and/or patient interface 150 can also include a $CO_2$ sensor 160. In FIG. 1, for example, the $CO_2$ sensor 160 is located near the elbow 162 of patient interface 150 or tubing 130. According to an embodiment, the $CO_2$ sensor 160 is in wired or wireless communication with controller 120. It should be noted that although $CO_2$ sensor 160 is depicted as an integral $CO_2$ sensor in FIG. 1, the sensor may be separate from the ventilator, tubing, or mask.

System 100 also includes a blower 180 with a motor, which generates flow and pressure for the system. The blower motor is controlled by a blower motor controller, which can control, for example, the speed of the motor. According to an embodiment, the blower motor is a component of the blower, which can include an impeller, housing, and motor. The flow and pressure of the system is determined in part by the speed of the blower motor, the activity of which in turn is controlled by the blower motor controller. The blower motor controller can be the same controller as controller 120, or can be a separate controller preferably in communication with controller 120. The controller can be any processor, and can be coupled with or otherwise in communication with any needed memory, power supply, I/O devices, control circuitry, and/or other devices necessary for operation of the system according to the embodiments described or otherwise envisioned herein.

According to an embodiment, system 100 uses both ambient air and a high-pressure gas source, such as an oxygen source, to produce the gas delivered to the patient. The gas source can be any gas source that might be utilized, such as surrounding environmental air, an oxygen tank, a nitrogen tank, mixtures thereof, as well as a very wide variety of other gas sources.

According to an embodiment, the non-invasive ventilation system 100 also includes a user interface (UI) 170. UI 170 includes graphical, textual and/or auditory information that the system presents to the user, such as a clinician, as well as the control sequences—such as keystrokes, computer mouse movements or selections, and/or touchscreen movements or selections, among other control sequences—that the user utilizes to control the system. In one embodiment, the UI 170 is a graphical user interface. For example, as shown in FIG. 1, UI 170 includes a display screen 172. Display screen 172 may include, for example, a touchscreen enabling the user to change one or more settings of the non-invasive ventilation system 100, as well as a graphical output that displays breathing and ventilation information to the user.

For example, according to an embodiment, user interface 170 includes an interface such as a button or switch that the user pushes, slides, switches, or otherwise activates in order to activate the $CO_2$ measurement. As another example, the display screen can include a touchscreen $CO_2$ measurement button or other input mechanism using touch, a stylus, or another selection mechanism. The user interface can also provide the user with options and variables for the $CO_2$ measurement routine, including the selection of the inspiratory positive airway pressure (IPAP) and/or expiratory positive airway pressure (EPAP) level during $CO_2$ measurement, as well as the time period or number of breaths over which the $CO_2$ measurement will occur.

According to an embodiment, user interface 170 and controller 120 operate cooperatively to configure the non-invasive ventilator to obtain a $CO_2$ measurement. The user interface 170 can be in communication with controller 120 such that when the user configures the system by selecting one or more functions or options, the controller 120 stores the information and activates the $CO_2$ measurement accordingly. For example, the user can select, via user interface 170, an EPAP level of 1 $cmH_2O$ for a period of two breaths during a $CO_2$ measurement that will be obtained immediately. The controller 120 receives the user input from the user interface and activates the $CO_2$ measurement. Alternatively, the user can select, via user interface 170, an EPAP level of 0 cmH$_2$O for a period of four breaths during a CO$_2$ measurement which will be obtained every 10 minutes. The controller 120 receives the user input from the user interface and activates a timing mechanism for the next CO$_2$ measurement. The user may also utilize the user interface to direct the controller to activate a CO$_2$ measurement if a selected condition is detected, such as a change in average breath rate. Accordingly, the controller 120 receives the information from the user interface 170 and begins monitoring for the triggering condition for CO$_2$ measurement.

Figure 2:
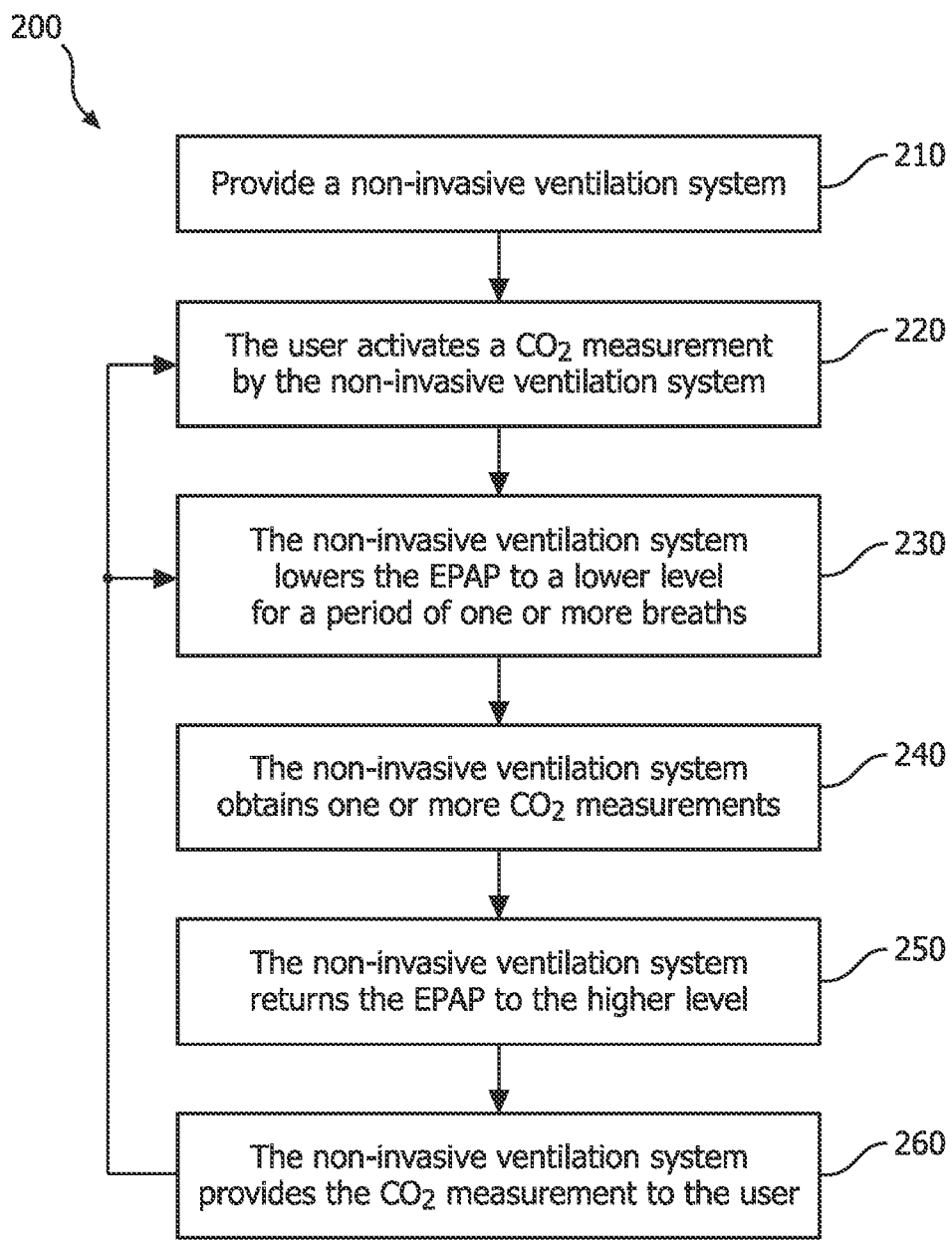
FIG. 2 is a flowchart of a method for measuring $CO_2$ using a non-invasive ventilator system, in accordance with an embodiment.

Referring to FIG. 2, in one embodiment, is a flowchart of a method 200 for measuring CO$_2$ in a non-invasive ventilator system. At step 210, a non-invasive ventilation system 100 is provided. The system is any of the non-invasive ventilation systems described or otherwise envisioned herein, and can include, for example, a controller 120, a blower 180, tubing 130, patient interface 150, and CO$_2$ sensor 160, among other components. Other embodiments are also possible.

At step 220 of the method, the user activates a CO$_2$ measurement from the patient. For example, a clinician may determine—after reviewing the patient's condition, lab results, or other information relevant to a CO$_2$ measurement—that a CO$_2$ measurement is needed immediately. As yet another example, the clinician may determine that a regular or periodic CO$_2$ measurement is necessary, and thus will configure the system to obtain a CO$_2$ measurement at regular or periodic intervals. The interval may be, for example, every 3 to 5 minutes, every hour, every few hours, or any other desired interval. The clinician may alternatively determine that a CO$_2$ measurement is necessary if a certain condition is triggered, such as a change in patient-triggered breathing or some other trigger.

According to an embodiment, the clinician can activate a CO$_2$ measurement using the UI 170. The non-invasive ventilator system receives a signal, such as a signal from the UI, comprising an instruction to obtain a CO$_2$ measurement from a patient. For example, the UI can include a button or switch that the user pushes, slides, switches, or otherwise activates in order to activate the CO$_2$ measurement. As another example, the display screen can include a touchscreen CO$_2$ measurement button or other input mechanism using touch, a stylus, or another selection mechanism. According to an embodiment, the button or touchscreen button activates a pre-programmed routine that lowers the EPAP to a predetermined level for a predetermined number of breaths before raising the EPAP back to normal levels. According to another embodiment, the UI allows the user to select one or both of an EPAP level and a number of breaths for the CO$_2$ measurement. For example, the clinician can select a pre-programmed CO$_2$ measurement program or setting that adjusts the EPAP level to one (1) cmH$_2$O for a period of two (2) breaths by the patient. According to an embodiment, the maximum number of breaths for a CO$_2$ measurement can be based on the low leak alarm setting of the non-invasive ventilator system, which can vary by platform.

The EPAP level is preferably set to a level equal to or greater than 0 cmH$_2$O and lower than 4 cmH$_2$O during expiration. In some systems or scenarios, a setting of one (1) cmH$_2$O during expiration, for example, provides positive pressure that prevents a mask flap—such as the anti-asphyxiation valve—from opening during CO$_2$ measurement. An open anti-asphyxiation valve would negatively affect the CO$_2$ measurement as exhaled gas from the patient will escape through the open valve before reaching the CO2 sensor. In contrast, in some systems or scenarios a setting of three (3) cmH$_2$O during expiration will push too much gas into the system and similarly negatively affect the CO$_2$ measurement.

At step 230 of the method, the non-invasive ventilation system 100 lowers the EPAP level for a period of one or more patient breaths. According to an embodiment, the controller 120 receives input from the user activating a pre-programmed CO$_2$ measurement routine and/or determining one or more settings of a CO$_2$ measurement routine. The controller can for example, execute a program stored in memory to accomplish the lowered EPAP. Since most non-invasive ventilator systems utilize flow from a blower 180 to control inspiratory and expiratory pressures, the controller 120 can send a control signal to the blower 180 to control or adjust the EPAP. To ensure that the routine includes only the prescribed number of patient breaths, the system includes a counting mechanism to determine how many breaths are given to or taken by the patient. For example, the controller 120 may include a timer and/or counter that tracks the number of breaths, or may use one or more of a pressure or airflow sensing to sense a patient breath.

The non-invasive ventilation system 100 can be configured to interrupt, disrupt, or otherwise adjust leak compensation in order to lower the EPAP level and obtain the CO$_2$ measurement. Obtaining a CO$_2$ measurement using the methods and systems described or otherwise envisioned herein may be especially important during periods of high leaks in the non-invasive ventilator system when a larger amount of gas is flowing from the ventilator to the patient in order to compensate for the large leak. This dilutes normal CO$_2$ measurements, since almost no exhaled flow may reach the CO$_2$ sensor, and thus increases the need for the CO$_2$ measurement embodiments described herein. Accordingly, the non-invasive ventilation system may include an override to deactivate or pause the leak compensation and allow for proper CO$_2$ measurements using the described embodiments.

At step 240 of the method, one or more CO$_2$ measurements are obtained. System 100 can include a standalone or integrated CO$_2$ sensor such as CO$_2$ sensor 160 is located near the elbow 162 of patient interface 150 or tubing 130 in FIG. 1. Alternatively, the CO$_2$ sensor can be a standalone sensor in wired or wireless communication with non-invasive ventilator system 100. The system, such as controller 120, sends a signal to the CO$_2$ sensor with instructions to obtain one or more CO$_2$ measurements during the period of lowered EPAP levels. In the case of a wireless standalone CO$_2$ sensor, the controller 120 may send a wireless signal to the standalone CO$_2$ sensor.

At step 250 of the method, the non-invasive ventilation system 100 returns the EPAP to its original pressure. According to an embodiment, the controller 120 determines that the lowered EPAP phase of the selected or pre-programmed CO$_2$ measurement routine is complete and that the EPAP should be returned to normal levels. Accordingly, the controller 120 sends a control signal to the blower 180 to control or adjust the EPAP.

According to an embodiment, in an automated or pre-programmed CO$_2$ measurement routine, the completion of the lowered EPAP phase or the return of the EPAP to normal levels can trigger a countdown to the next lowered EPAP phase. Accordingly, controller 120 may include, for example, a timer and/or clock that determines when the next CO$_2$ measurement is required. In other systems, CO$_2$ measurements are only obtained in direct response to a user's selection or activation.

At step 260 of the method, the non-invasive ventilation system 100 provides the output of the $CO_2$ measurement to the user. This output could be provided, for example, via UI 170 and display screen 172. The $CO_2$ measurement can be presented as a percentage, a concentration, or any other measurement.

If the system is executing a pre-programmed $CO_2$ measurement routine, the method can return to step 230 at the appropriate time. For example, the clock or timer of controller 120, or another clock or timer of the system, can determine that a predetermined number of breaths or amount of time has expired, and that, according to the pre-programmed routine, a new $CO_2$ measurement is necessary. Alternatively, the system can return to normal EPAP levels and await a user instruction to activate a $CO_2$ measurement at step 220.

Figure 3:
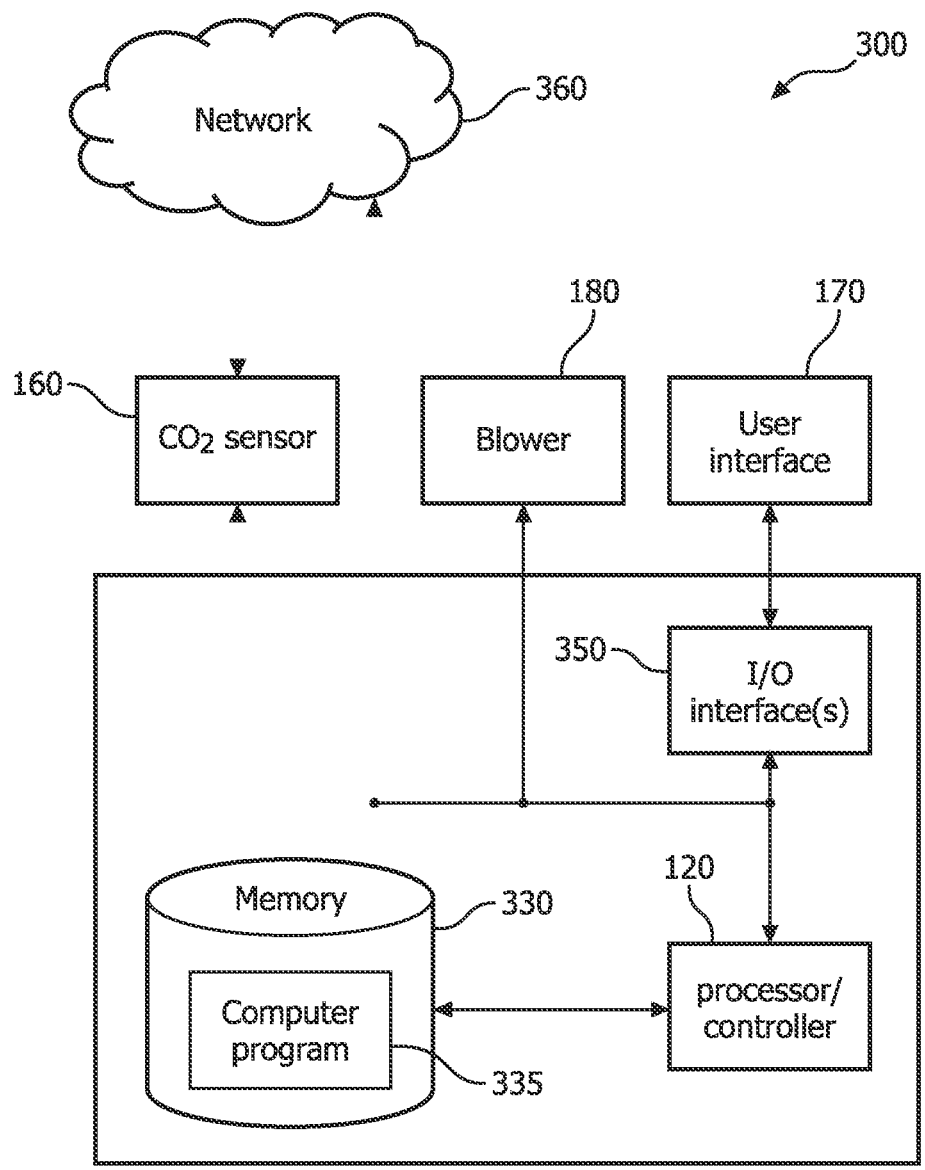
FIG. 3 is a schematic representation of a computer system of a non-invasive ventilator configured to obtain $CO_2$ measurements, in accordance with an embodiment.

Referring to FIG. 3, in one embodiment, is a block diagram of a computer system 300, such as a computer system of ventilator system 100, in accordance with an embodiment. The computer system 300 includes, for example, a controller 120, memory 330, and I/O interface 350, among other possible components.

Controller 120 can be a processor, an application specific integrated circuit (ASIC), a system on chip (SOC), and/or a field-programmable gate arrays (FPGA), among other types of controllers. The controller may be implemented with or without employing a processor, and also may be implemented as a combination of dedicated hardware to perform some functions and a processor (e.g., one or more programmed microprocessors and associated circuitry) to perform other functions. According to an embodiment, the controller 120 is coupled with or otherwise in communication with storage media such as memory 330. In some implementations, the storage media may be encoded with one or more computer programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. According to an embodiment, memory 330 may include one or more computer program products 335 configured to execute one or more embodiments of the $CO_2$ measurement system and method.

Computer system 300 communicates with one or more external devices, such as a $CO_2$ sensor or measurement device 160, blower 180, and/or user interface 170, all described herein. Communication with any one of these devices can be achieved via an input/output (I/O) interface 350. Communication can also or alternatively occur with any one of these devices via a direct wired connection, or via one or more networks 360, for example, the Internet, a local area network, a wide area network, and/or a wireless network. For example, according to an embodiment the $CO_2$ sensor or measurement device 160 is an external device, and the computer system 300 communicates via network 360. Alternatively, the $CO_2$ sensor or measurement device is an integrated component of the system and the computer system communicates via a direct connection.

Figure 4:
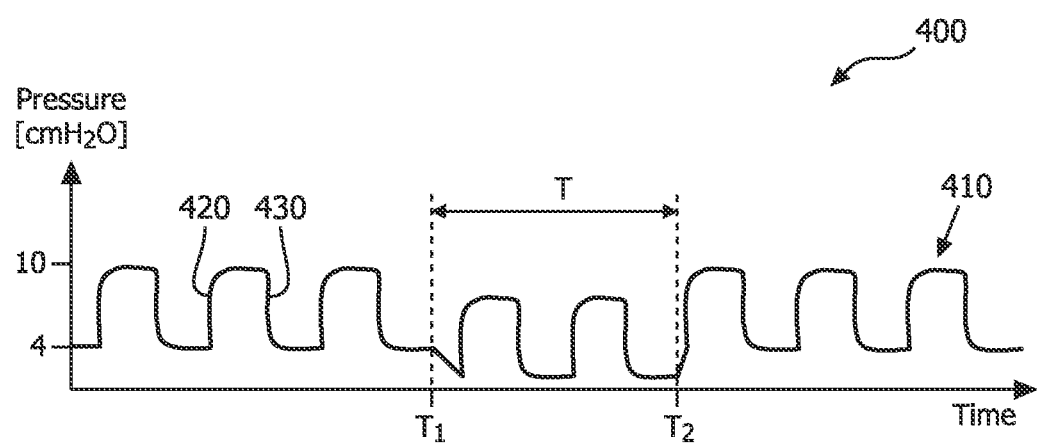
FIG. 4 is a graph showing a pressure waveform for a non-invasive ventilator system, in accordance with an embodiment.

Referring to FIG. 3, in one embodiment, is a graph 400 showing an exemplary non-invasive ventilator pressure curve 410 in $cmH_2O$. The curve illustrates the pressure applied to the patient with rising portions 420 of the curve to create the prescribed inspiratory positive airway pressure (IPAP) to the patient's respiratory system during inhalation, and on falling portions 430 of the curve when exhalation begins to create the prescribed expiratory positive airway pressure (EPAP) to the respiratory system during exhalation. As shown in the curve in FIG. 4, the IPAP is approximately 10 $cmH_2O$, and the EPAP is approximately 4 $cmH_2O$. According to an embodiment, the pressure is controlled by controlling the blower as described herein.

According to an embodiment, at some time prior to time $T_1$, the user activates the system to obtain a $CO_2$ measurement from the patient. For example, the clinician may determine that a $CO_2$ measurement is needed immediately, or may determine that a regular or periodic $CO_2$ measurement is necessary, and thus will configure the system to obtain a $CO_2$ measurement at regular or periodic intervals. At time $T_1$, the non-invasive ventilation system 100 lowers the IPAP and/or EPAP levels for a period of one or more patient breaths. According to an embodiment, the controller 120 applies a signal to the blower 180 to establish the lower prescribed IPAP pressure during inhalation and the lower prescribed EPAP pressure during exhalation. As shown in the curve in FIG. 4, the lowered IPAP is approximately 7 $cmH_2O$, and the lowered EPAP is approximately 1 $cmH_2O$, for a period of two breaths during time T.

During time T, one or more $CO_2$ measurements are obtained. System 100 can include a standalone or integrated $CO_2$ sensor such as $CO_2$ sensor 160 is located near the elbow 162 of patient interface 150 or tubing 130 in FIG. 1. Alternatively, the $CO_2$ sensor can be a standalone sensor in wired or wireless communication with non-invasive ventilator system 100. The system, such as controller 120, sends a signal to the $CO_2$ sensor to obtain one or more $CO_2$ measurements during the period of lowered EPAP levels. In the case of a wireless standalone $CO_2$ sensor, the controller 120 may send a wireless signal to the standalone $CO_2$ sensor.

At time $T_2$, the non-invasive ventilation system 100 raises the IPAP and EPAP levels to pre-measurement levels. As shown in the curve in FIG. 4, the IPAP level is returned to approximately 10 $cmH_2O$, and the EPAP is returned to approximately 4 $cmH_2O$. According to an embodiment, the controller 120 determines that the lowered EPAP phase of the selected or pre-programmed $CO_2$ measurement routine is complete and that the EPAP should be returned to normal levels. Accordingly, the controller 120 sends a signal to the blower 180 to control or adjust the EPAP.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for measuring a patient's expired $CO_2$ level in a non-invasive ventilator system while maintaining a positive inspiratory pressure, the non-invasive ventilator system comprising a $CO_2$ sensor, the method comprising the steps of:
   receiving, by the non-invasive ventilator system, a first control signal comprising an instruction to obtain a $CO_2$ measurement from a patient for a user-defined first time period;
   adjusting, by the non-invasive ventilator system, leak compensation during the user-defined first time period;
   lowering, by the non-invasive ventilator system in response to the first control signal for the user-defined first time period comprising one or more breaths, (i) an expiratory positive airway pressure from a first, higher level to a second, lower level, and (ii) an inspiratory positive airway pressure of the non-invasive ventilatory system from a third, higher level to a fourth, lower level;
   obtaining, by the $CO_2$ sensor, a $CO_2$ measurement during the user-defined first time period; and
   returning, after termination of the user-defined first time period, the expiratory positive airway pressure to the first, higher level and the inspiratory positive airway pressure to the third, higher level.

2. The method of claim 1, wherein the first control signal comprising the instruction to obtain the $CO_2$ measurement from the patient is received from a user.

3. The method of claim 1, wherein the step of lowering the expiratory positive airway pressure from the first, higher level to the second, lower level comprises sending a second control signal to a blower of the non-invasive ventilator.

4. The method of claim 1, further comprising the step of sending the first control signal from a controller of the non-invasive ventilator system to the $CO_2$ sensor, the first control signal comprising instructions to obtain the $CO_2$ measurement during the first time period.

5. The method of claim 1, wherein the second, lower level is approximately 1 $cmH_2O$.

6. The method of claim 1, wherein the user-defined first time period is at least two breaths.

7. The method of claim 6, wherein the user-defined time period is based on a low leak alarm setting of the non-invasive ventilator system.

8. The method of claim 1, wherein the step of receiving further comprises configuring the non-invasive ventilator system to obtain the $CO_2$ measurement at a user-defined periodic interval.

9. The method of claim 1, wherein the $CO_2$ sensor of the non-invasive ventilator system is integrated.

10. A non-invasive ventilator configured to measure a patient's expired $CO_2$ level while maintaining a positive inspiratory pressure, the non-invasive ventilator comprising:
    a user interface configured to receive, from a user, a signal comprising an instruction to obtain a $CO_2$ measurement from the patient during a user-defined first time period comprising-one or more breaths;
    a $CO_2$ sensor configured to obtain one or more expired $CO_2$ measurements from the patient during the user-defined first time period the one or more expired $CO_2$ measurements including the $CO_2$ measurement; and
    a controller in communication with the $CO_2$ sensor, the controller configured to: lower, in response to the signal for the user-defined first time period, (i) an expiratory positive airway pressure from a first, higher level to a second, lower level, and (ii) an inspiratory positive airway pressure of the non-invasive ventilatory system from a third, higher level to a fourth, lower level; direct the $CO_2$ sensor to obtain the $CO_2$ measurement during the user-defined first time period; track the one or more breaths; and return, after termination of the user-defined first time period, the expiratory positive airway pressure to the first, higher level and the inspiratory positive airway pressure to the third, higher level.

11. The non-invasive ventilator of claim 10, wherein the controller is configured to lower the expiratory positive airway pressure by controlling an activity of a blower of the non-invasive ventilator.

12. The non-invasive ventilator of claim 10, wherein the $CO_2$ sensor is an integrated sensor located proximate to a patient interface.

13. The non-invasive ventilator of claim 10, wherein the signal further comprises instructions to obtain the $CO_2$ measurement at a user-defined periodic interval during patient-triggered breaths.

14. A controller of a non-invasive ventilator system configured to measure a patient's expired $CO_2$ level while maintaining a positive inspiratory pressure, the controller configured to perform steps comprising:

receive, from a user interface of the non-invasive ventilator system, a first control signal comprising an instruction to obtain a $CO_2$ measurement from a patient for a user-defined first time period;

lower, in response to the first control signal for the user-defined first time period comprising one or more breaths, (i) an expiratory positive airway pressure of the non-invasive ventilator system from a first, higher level to a second, lower level, and (ii) the inspiratory positive airway pressure of the non-invasive ventilator system from a third, higher level to a fourth, lower level, wherein the controller is configured to send a second control signal to a blower of the non-invasive ventilator system;

send the first control signal to a $CO_2$ sensor of the non-invasive ventilator system, the first control signal comprising instructions to obtain the $CO_2$ measurement during the user-defined first time period;

track the one or more breaths; and return, after termination of the user-defined first time period, the expiratory positive airway pressure to the first, higher level and the inspiratory positive airway pressure to the third, higher level.

15. The controller of claim 14, wherein the second, lower level is approximately 1 $cmH_2O$.

16. The controller of claim 14, wherein the first time period is approximately two breaths.

* * * * *